United States Patent [19]

Viallet et al.

[11] Patent Number: 5,214,029
[45] Date of Patent: May 25, 1993

[54] INHIBITION OF MALIGNANT CELLS HAVING $G_{M1}$ GANGLO-SIDE SITES BY ADMINISTRATION OF CHOLERA TOXIN

[76] Inventors: Jean Viallet, 723 Owens St., Rockville, Md. 20850; Edward Sausville, 1114 Nora Dr., Silver Spring, Md. 20904; John D. Minna, 8520 Howell Rd., Bethesda, Md. 20817

[21] Appl. No.: 767,578

[22] Filed: Sep. 30, 1991

Related U.S. Application Data

[63] Continuation of Ser. No. 438,643, Nov. 20, 1989, abandoned.

[51] Int. Cl.$^5$ ............... A61K 39/02; A61K 35/74
[52] U.S. Cl. ................................ 514/12; 435/177;
435/188; 514/2; 514/8; 530/825
[58] Field of Search ............... 435/177, 188; 514/2, 514/12, 8; 520/825

[56] References Cited

PUBLICATIONS

Cho-Chung et al., *Cancer Res.* 43, 1473-1476 (1987).
Kurosky et al., "Covalent Structure of the Chain of Cholera Enterotoxin" J. of Biological Chemistry, vol. 252, No. 20, Oct. 25, pp. 7257-7284, 1977.
Lai, "Determination of the Primary Structure of Cholera Toxin B Subunit" J. Biological Chemistry, vol. 252, No. 20, Oct. 25, pp. 7249-7256, 1977.
Yoon Sang Cho-Chung et al., "Arrest of Hormone-Dependent Mammary Cancer Growth In Vivo and In Vitro by Cholera Toxin", Cancer Research 43, 1473-1476, Apr. 1983.
Meister, ed., Advances in Enzymology and Related Areas of Molecular Biology, vol. 61, 1988 Moss et al. "ADP-Ribosylation of Guanyl Nucleotide-Binding Regulatory Proteins by Bacterial Toxins" pp. 303-379.
Carney et al., "Establishment and Identification of Small Cell Lung Cancer Cell Lines Having Classic and Variant Features", Cancer Research vol. 45, Jun. 1985, pp. 2913-2923.
Fischer et al., "The Bombesin Receptor is Coupled to a Guanine Nucleotide-binding Protein which is Insensitive to Pertussis and Cholera Toxins", J. Biological Chemistry, vol. 263, No. 6 Feb. 25, pp. 2808-2816, 1988.
Biffen et al., "Polyphosphoinositide Labeling in Rat Liver Plasma Membranes is Reduced by Preincubation with Cholera Toxin", J. Biological Chemistry, vol. 262, No. 16, Jun. 5, pp. 7744-7750, 1987.
Urumow et al., "Evidence for a Cholera-Toxin-Sensitive G-Protein Involved in the Regulation of Phosphatidylinositol 4-Phosphate Kinase of Rat Liver Membranes", Biochemica et Biophysica Acta. 972 (1988) 232-238.
Holmgren et al., "In Vivo Moldulation of Intracellular cAMP and cell Growth of a Lymphatic Tumour in Mice by Cholera Toxin", Experimental Cell Research 108 (1977) 31-39.
Pierce et al., "Systemic Effects of Parenteral Cholera Enterotoxin in Dogs", J. Law. Clin. Med. 79: 145-158, 1972.
Green, "Cyclic AMP in Relation to Proliferation of the Epidermal Cell: a New View", Cell, vol. 19, 801-811, Nov. 1978.
Trepel et al., "A Novel Bombesin Receptor Antagonist Inhibits Autocrine Signals in a Small Cell Lung Carcinoma Cell Line," Nov. 15, 1988, Academic Press, Inc. #0006-291X/88.
Chopra et al., "Effects of Insulin, Transferrin, Cholera Toxin, and Epidermal Growth Factor on Growth and Morphology of Human Fetal Normal Colon Epithelial Cells", Gasteroenterology 1987, 92 891-904.
Cuttita et al., "Bombesin-like peptides can Function as Autocrine Growth Factors in Human Small-Cell Lung Cancer", Nature (reprint), Macmillan Journals Ltd. 1985.

(List continued on next page.)

*Primary Examiner*—Howard E. Schain
*Attorney, Agent, or Firm*—Cushman, Darby & Cushman

[57] ABSTRACT

The invention is to a method of treating malignancies with cholera toxin after determining if labelled beta subunit cholera toxin binds to the tissue.

4 Claims, 10 Drawing Sheets

OTHER PUBLICATIONS

Mekalanos et al., "Cholera Toxin Genes: Nucleotide Sequence, Deletion Analysis and Vaccine Development", Nature, vol. 106, 8 Dec. 1987, pp. 551–557.

Lockman et al., "Nucleotide Sequence Analysis of the A2 and B Subunits of *Vibrio cholerae* Enterotoxin", J. Biological Chemistry, vol. 258, No. 22, Nov. 25, pp. 13722–13726, 1983.

Nakanishi et al., "Insulin–like Growth Factor-1 Can Mediate Autocrine Proliferation of Human Small Cell Lung Cancer Cell Lines In Vitro", J. of Clinical Investigation, Inc. vol. 82, KJuly 1988, 354–359.

Taylor-Papadimitriou et al. "Cholera Toxin and Analogues of Cyclic AMP Stimulate the Growth of Cultured Human Mammary Epithelial Cells", J. of Cellular Physiology 102-137-321 (1980).

Carmichael et al., "Evaluation of a Tetrazolium-based Semiautomated Colorimetric Assay: Assessment of Chemosensitivity Testing", Cancer Research 47, 936–942, Feb. 15, 1987.

Lechner et al., "Clonal Growth of Epithelial Cells from Normal Adult Human Bronchus", Cancer Research 41, 2294–2304, Jun. 1981.

Namberg et al., "Temporal Relationship Between Inositol Polyphosphate Formation and Increases in Cytosolic $Ca^{2+}$ in Quiescent 3T3 Cells Stimulated by Platelet-Derived Growth Factor, Bombesin and Vasopressin", Imperial Cancer Research Fund, London, IRL Press Limited, Oxford, England, pp. 2741–2746.

Swope et al., "The Biphasic Stimulation of Insulin Secretion by Bombesin Involves Both Cystolic Free Calcium and Protein Kinase C", Biochem. J. (1988) 253, 193–202 (printed in Great Britain).

Fain et al., "Evidence for Involvement of Guanine Nucleotide-binding Regulatory Proteins in the Activation of Phospholipases by Hormones",FASEB, J. 2: 2569–2574; 1988.

Jane B. Trepel, et al. Modulation of bombesin-induced phosphatidylinositol hydrolysis in a small-cell lung--cancer cell line. Biochem. J. (1988) 255, 403–410.

Viallet et al. Abstract related to the inhibition of growth of human small cell lung cancer by cholera toxin. Distributed at the Biology of Cellular Transducing Signals Symposium on May 8, 1989.

Clinical Research Abstract (vol. 36, 501-A, 1988) discloses cholera toxin sensitivity of a bombesin-responsive small cell lung carcinoma cell line.

FIG. 1A

% SURVIVAL AT 7 DAYS (MEAN+/−SE) vs TOXIN CONCENTRATION (ug/ml) — CT and CT BETA

FIG. 1B

% SURVIVAL AT 7 DAYS (MEAN+/−SE) vs TOXIN CONCENTRATION (ug/ml) — CT and CT BETA

NCI-H345  NCI-H82

NCI-H345  NCI-H417

INHIBITION OF MALIGNANT CELLS HAVING $G_{M1}$ GANGLO-SIDE SITES BY ADMINISTRATION OF CHOLERA TOXIN

This is a continuation of application Ser. No. 07/438,643, filed on Nov. 20, 1989, now abandoned.

SUMMARY OF THE INVENTION

This invention relates to treatment of certain malignancies characterized by presence of $G_{M1}$ ganglioside on the cell membrane. While it had previously been known that growth of some malignant cells could be inhibited by exposure to cholera toxin (CT), the use of that toxin as a therapeutic agent was not previously considered as a practical approach to treatment. Part of the difficulty arose from lack of means of predicting which malignancies would respond to such treatment. The instant invention provides means of identifying malignancies that would respond to treatment with cholera toxin along with dosage requirements and means of administration of the active agent.

BACKGROUND OF THE INVENTION

Cholera has been known for many centuries as a deadly disease whose victims die after bouts of severe diarrhea from dehydration and malnutrition. The causative organism replicates in the intestine. In response to the toxins produced, the intestine excretes large amounts of water. However, in tissue culture, cholera toxin stimulates growth of epithelial cells. (Taylor-Papadimitriou, et al., *J. Cell. Physiol.* 102: 317-321 (1980) and Chopra, et al., *Gastroenterology* 92: 891-904 (1987)) It had, furthermore, been known that growth of some malignant cells was inhibited by treatment with cholera toxin. (Cho-Chung, et al. *Cancer Res.* 43: 1473-1476 (1987)). It was assumed, by Cho-Chung and her co-workers that the response to the toxin was due to stimulation of the intracellular cAMP system. (Her work was primarily concerned with mammary cancers and lymphomas.) However, the work of Cho-Chung did not lead to a means of treating malignancies in patients, since no means of predicting efficacy in treating a particular patient could be predicted and no method for therapeutic treatment was described.

The treatment of human small cell lung carcinoma (SCLC), has heretofore been difficult. The disease accounts for about 30% of all lung cancers. The malignancy is characterized by several neuroendocrine features which include the elaboration of peptide hormones such as gastrin-releasing peptide (GRP). The growth of the cells in serum free conditions is often enhanced in the presence of bobesin.

Previous studies in murine fibroblasts, SCLC, anterior pituitary, and rat insulinoma cells have shown that binding of GRP to its receptor results in activation of phospholipase-C, increased phosphatidylinositol (PI) turnover, release of calcium from internal stores, increase of intracellular free calcium ($[Ca2+]i$), and activation of protein kinase-C. Thus, an understanding of bombesin or GRP stimulation of SCLC growth requires the definition of elements important in the process of bombesin-mediated signal transduction.

As previous studies in multiple tissues have suggested that hormonal activation of phospholipase C may be mediated by a guanine nucleotide binding protein (G protein), a study was begun to evaluate the effects of bacterial toxins known to modulate G protein function on GRP stimulated signal transduction pathways in the SCLC cell line NCI-H345. It was found that pretreatment with cholera toxin (CT) at 1 ug/ml for 18 hours resulted in a substantial inhibition in basal and GRP stimulated intracellular calcium and inositol trisphosphate (IP3), as well as the production of GRP stimulated inositol monophospates.

The classical biology of CT did not readily account for the observations of Cho-Chung and others. CT binds to a cell surface glycolipid, the $G_{M1}$ ganglioside, through its beta subunit. After internalization, the pentameric beta subunits are cleaved from the catalytic alpha subunit which in turn stimulates the ADP ribosylation of Gas, the stimulatory G protein coupled to adenylate cyclase, leading to an inhibition of its GTPase activity. This non reversible GTP-bound state in turn activates adenylate cyclase and leads to an elevation of intracellular cAMP levels. However, reproduction of the effects of CT on GRP mediated signal transduction using other maneuvers to increase intracellular cAMP was not possible.

FIGURE LEGENDS

FIG. 1 Cholera toxin inhibits the growth of GM1 ganglioside bearing SCLC cell lines. (A), (B), (C) and (D) shows cell survival after 7 days of incubation with CT or the b subunit alone. (E) shows a thin layer chromatogram of whole cell lipid extracts showing abundant binding of b subunit-peroxidase conjugate to the sensitive cell lines with no evidence of binding to the resistant one.

FIG. 2, A and B Effect of CT on the morphology of NCI-H345. Overnight incubation with CT at 1 mg/ml results in a loss of the typical ruffled cytoplasmic border (see arrows). Cells are viable by Trypan blue exclusion. (m) indicates a mitosis.

FIG. 3 CT substrates in SCLC cell lines. (A) shows an immunoblot of a bovine brain cholate extract (BB) and SCLC crude membrane preparation using an anti-Gs specific antibody. (B) and (C) shows ADP-ribosylation substrates of CT in CT sensitive and resistant cell lines. The only apparent substrates co-migrate with authentic Gs seen in panel (A).

FIG. 6 Effect of CT on agonist induced increase in $[Ca++]i$. NCI-H345 cells were treated with CT 1 mg/ml × 18 hours, then loaded with Quin 2. When compared to control cells, CT pretreatment leads to an inhibition of $[Ca++]i$ increase in response to T4B 100 nM, vasopressin 1 mM and FCS 0, 25%.

FIG. 7, A, B, C, and D, Effect of pretreatment with 1 ug/ml of CT (but not the isolated b-subunit of CT) for 18 hours was studied by determining extent of $[^{32}PO_4]$ incorporated into PI, PIP, and $PIP_2$ in the cell lines.

DETAILED DESCRIPTION OF THE INVENTION

It is the purpose of this invention to provide a means of identifying malignancies that can be treated using cholera toxin.

It is a further purpose of this invention to provide a method of treating patients suffering from malignancies which are responsive to cholera toxin therapy.

MATERIALS AND METHODS

Reagents and Cell Culture

Cholera toxin (CT), the beta subunit of CT, and horse-radish peroxidase conjugated to the beta subunit of CT were from List Biologicals. The CT can also be obtained from the strain deposited in the ATCC having accession number 25870. [Tyr$^4$]—bombesin and [Arg$^8$]-vasopressin were from Peninsula. [3-(4,5-dimethylthiazole-2-yl)-2,5-diphenyltetrazolium bromide](MTT), Quin 2 AM, forskolin, G$^M{_1}$ ganglioside, phosphatidylinositol (PI), phosphatidyl-4-phosphate(PIP), phosphatidylinositol-4,5-bisphosphate(PIP$_2$), GTP, ATP, diaminobenzidine and thymidine were from Sigma. [$^{125}$I]-protein A and [$^{32}$P]-NAD were from New England Nuclear. [$^3$H]inositol and cAMP radiobinding assay kits were from were from Amersham.

NCI-H345, NCI-H209, NCI-H82, and NCI-N417 are established human SCLC cell lines derived from patient material and maintained in RPMI-1640 supplemented with 5 ug/ml insulin, 10 ug/ml transferrin, and 30 nM sodium selenite (R-SIT) in the presence of penicillin, streptomycin, and fungizone.

MTT Assay for Cell Growth

Estimation of cell growth was accomplished by the method of Carmichael (*Cancer Res.* 47: 936–942 (1987)). Ninety-six well plates receive 10–30,000 cells/well in 180 uL. The agent to be tested is added 12–15 hours later in 20 uL of medium. After seven days of incubation, 50 uL of 2 mg/ml solution of MTT is added and incubated at 37° C. for four hours, after which the cells are sedimented, the medium withdrawn, and the colored MTT reduction product estimated by absorbance at 540 nm in an ELISA reader after dissolving in dimethylsulfoxide.

G$_{M1}$ Ganglioside Expression in SCLC

Cells were washed in PBS and 2×10$^6$ cells lysed in 1.4 ml of 1:1 CHCl$_3$:CH$_3$OH(1:1). These were stored overnight at 4° C., solid residue removed, 1 ml dried, redissolved in 30 uL of CHCl$_3$:CH$_3$OH(1:1), applied to Bakerflex plastic-backed sheets, and chromatographed in CHCl$_3$:CH$_3$OH:0.25% KCl (60:35:6). The sheet was air-dried, wet with 1% polyvinylpyrrolidine in PBS for 40 min at 37° C. with gentle agitation. The beta subunit of CT conjugated to hoseradish peroxidase (200 ng/30 ml) was added at 37° C. for 40 min with mild agitation. The sheets were washed in PBS three times, and developed by incubation with diaminobenzidine (10 mg/30 cc of 0.05M Tris pH 7.6) plus 0.1 ml of 30% H$_2$O$_2$.

When testing patient tissue, the labelled subunit of CT can be applied directly to the tissue in any manner appropriate for use with the label used in the particular test.

Cyclic AMP Assay

At the indicated times after addition of drug or toxin, cells were centrifuged, washed in PBS, resuspended in 750 uL of 1 mM Tris pH 7.4, 4 mM EDTA, sonicated and an aliquot removed for protein determination. The samples were then boiled for 3 min, clarified, and stored at −70° C. until assay exactly as described in the Amersham cyclic AMP radiobinding assay kit. Protein content was determined using the Bio Rad assay.

Detection of G-Proteins in SCLC

Antisera to Gs, Gi isoforms, and Go were provided by Dr. Allen Spiegel, NIH. Western blots of SCLC whole cell lysates were prepared, washed, and detected by [$^{125}$I]-protein A.

Detection of CT Substrates in SCLC

CT substrates were detected in SCLC membranes by ADP-ribosylation. Crude membranes were prepared after the cells were washed once in 0.015M Na phosphate, 0.15M NaCl, pH 7.0(PBS), resuspended in 0.01M Tris pH 7.4, 0.1 mM EDTA, 2 uM leupeptin, 1 ug/ml aprotinin, and 1 ug/ml soybean trypsin inhibitor. The cells were disrupted by 30–40 strokes of a Teflon/glass homogenizer. Nuclei and unbroken cells were removed by centrifugation for 10 min at 800 rpm. The supernatant was centrifuged for 30 min in a JA 20 rotor at 20,000 rpm in a Sorvall centrifuge. The pellet was washed in 5 mM Hepes pH 7.4 and recentrifuged. The ADP ribosylation was conducted at 32° C. for 30 min in 0.1M K phosphate pH 7.2, 1 mM ATP, 20 mM thymidine, 2.5 mM MgCl2, 5 mM DTT, 40 ug/ml CT, 100 ug of membrane protein estimated by the BioRad assay, 0.8–3.2 uM [$^{32}$P]-NAD (30 Ci/mmole) with or without 0.2 mM GTP. The incubation was stopped by addition of 20 uL of 100% trichloroacetic acid (TCA), maintained at 4° C. for one hour, sedimented, and the pellets washed successively with 2% TCA, followed by three washes with water-saturated ether. Proteins were dissolved in Laemmli sample buffer with urea and 2-mercaptoethanol and SDS-polyacrylamide electrophoresis (PAGE) conducted. ADP-ribosylated proteins were detected by autoradiography of the dried gel.

Phosphatidylinositol Turnover and Mobilization of Calcium

SCLC were labelled for 5–6 d in R-SIT formulated without unlabelled inositol but which contained 5 uCi ml of [$^3$H]-inositol(16 Ci/mmole). CT was added for the time indicated in the Figure legends. After washing the cells and stimulation with agonists, inositol phosphates were separated. SCLC were loaded with quin 2AM, stimulated with agonists, and [Ca$^{2+}$]i measured by the change in recorded fluorescence.

[$^{125}$I-TYR$^4$]-Bombesin Binding to SCLC

Preparation of [$^{125}$I-Tyr$^4$]-bombesin and binding to whole SCLC cells was accomplished by the method of Trepel, et al. (*Bioghys. res. comm.* 156: 1383–1389 (1988)).

Phospholipid Synthesis in SCLC

After treatment with CT for 18–20 hours, SCLC were washed in Hepes buffered saline (140 mM NaCl, 5 mM KCl, 5 mM glucose, 1 mM CaCl$_2$, 1 mM MgCl12, 0.02M Hepes pH 7.4 and resuspended in triplicate in the same buffer at 1–5×10$^6$ cells/sample with 100 uCi of [$^{32}$PO$_4$] for 15 min. The cells were pelleted at 10,000×g for eight sec, the medium aspirated, and the cells lysed with 2 ml of CHCl$_3$:CH$_3$OH:conc HCl(2:1:0.01). The samples were vortexed vigorously and incubated at 37° C. for 20 min. Solid material was pelleted by centrifugation for 10 min at 10,000×g, the liquid phase removed to a fresh tube, and 0.4 ml of 1M HCl added to separate the phases. After removal of the aqueous phase, the lipid phase was washed twice with $CHCl_3:CH_3OH:1M$ HCL(3:48:47), dried, and redissolved in a small volume of $CHCl_3$ to which standard PI, PIP, and $PIP_2$ had been added. The sample was chromatographed on Silica gel thin layers which had been activated by prior spraying with 1% K oxalate and heating to 90° C. for 10 min. The chromatogram was developed in $CHCl_3:CH_3OH$: 4M $NH_4OH$(9:7:2), lipids localized by exposure to I2 vapors, and [$^{32}PO_4$] determined by scintillation counting.

Results. (Inhibition of SCLC Growth by CT.)

Figure 1A:
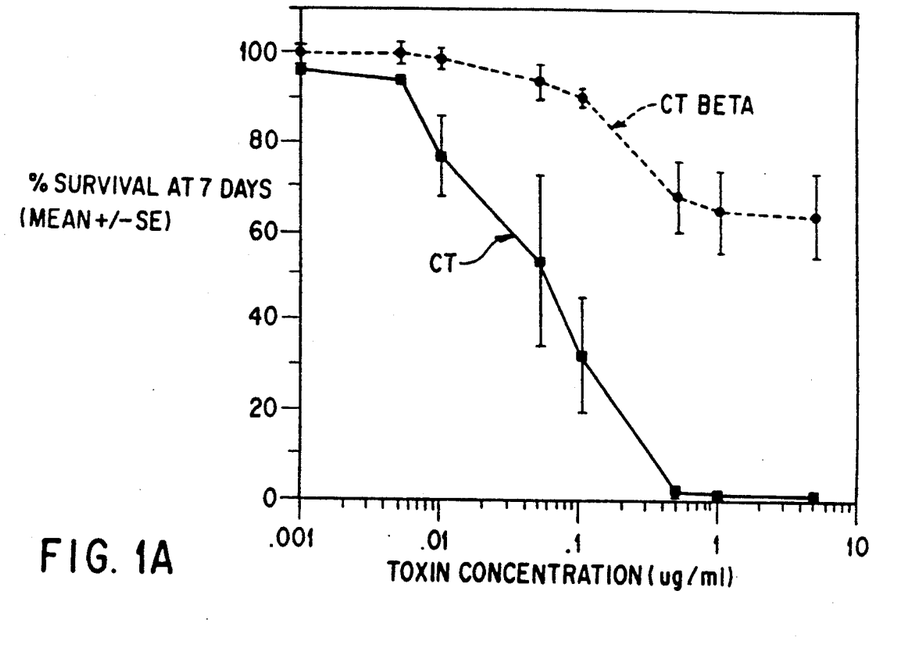
Figure 1B:
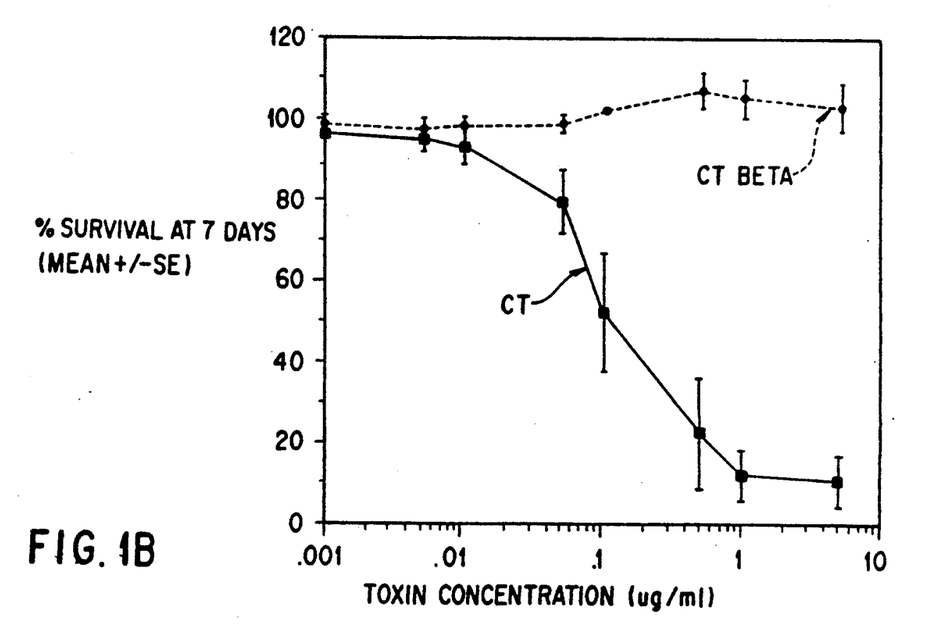
Figure 1C:
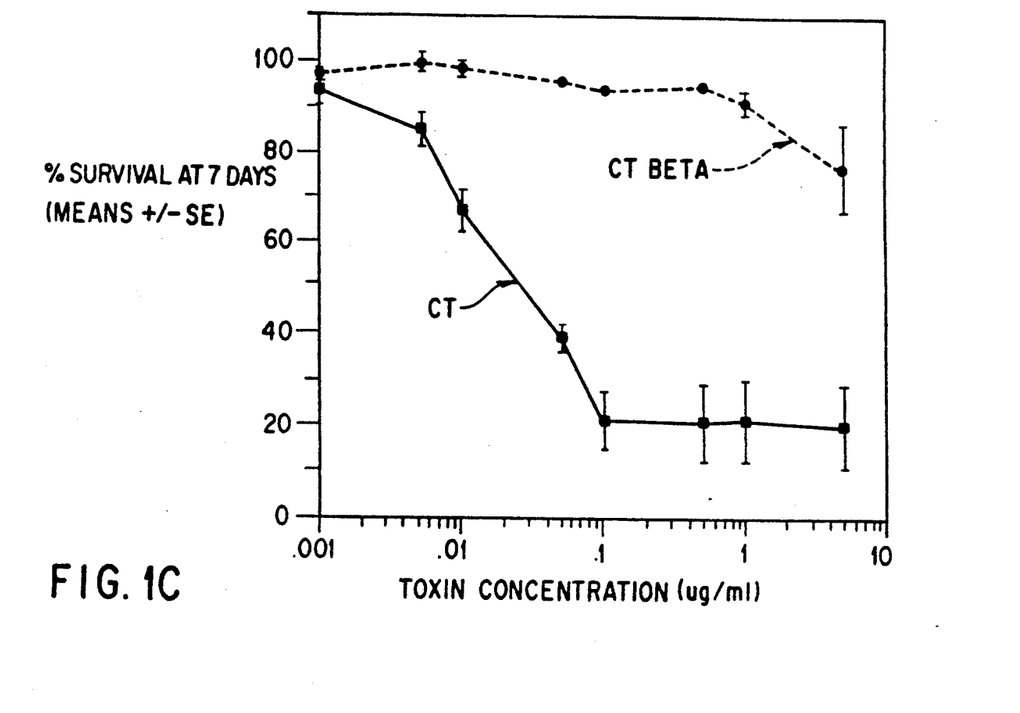
Figure 1D:
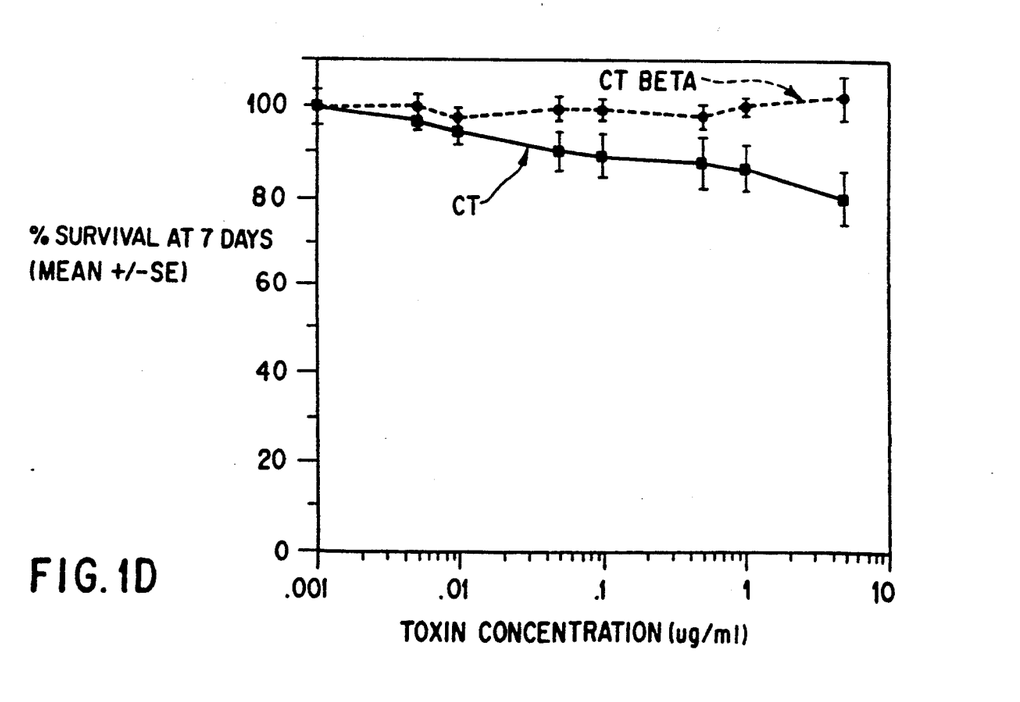

An assessment of the global impact of CT on SCLC biology was made by evaluating effect of CT on the growth of several SCLC cell lines. Dramatic inhibition of the survival of ¾ cell lines tested was found (NCI-H82, H209 and H345) with IC 50's ranging from 27 to 242 mg/ml (see FIG. 1-A, B and C) was found. In contrast, cell line NCI-N417 was quite resistant to the effects of CT at concentrations up to 5 ug/ml (see FIG. 1D). CT beta alone had no effects on the growth of any of these cell lines, nor had a control buffer of tris, EDTA, Na Cl and Na azide, corresponding to the final concentrations present in the CT and CT beta solutions (data not shown). In addition, these data were reproduced using a CT formulated without Na azide. Growth inhibition by CT was abrogated by inactivating the toxin by boiling prior to the experiment.

Figure 1E:
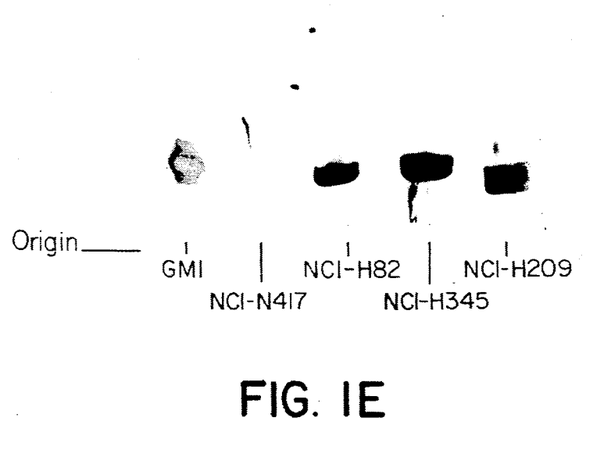

It was found that expression of the cell surface receptor for CT, $G_{M1}$ ganglioside, was the basis for differential sensitivity to this toxin. NCI-N417 lacked expression of $G_{M1}$ ganglioside on the cell surface. (FIG. 1E shows that the three CT-sensitive SCLC (NCI-H345, NCI-H209, and NCI-H82) all had easily detectable $G_{M1}$ ganglioside expression, whereas the CT-resistant SCLC cell line NCI-N417 did not.)

Figure 2A:
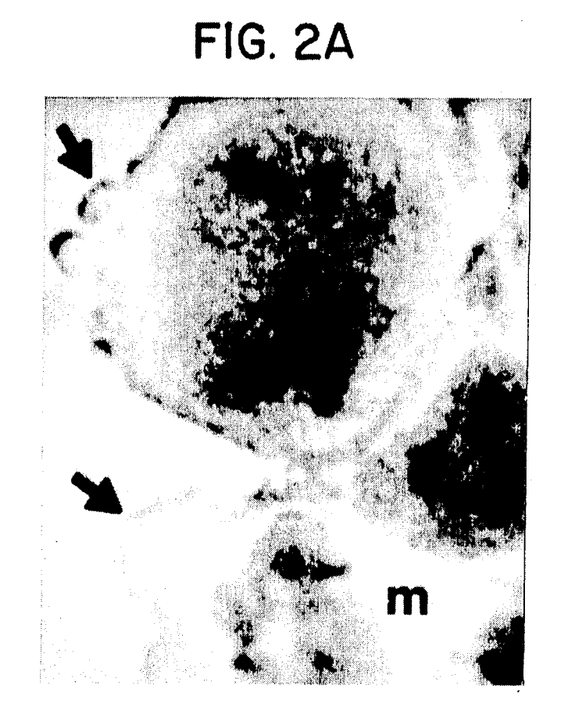
Figure 2B:
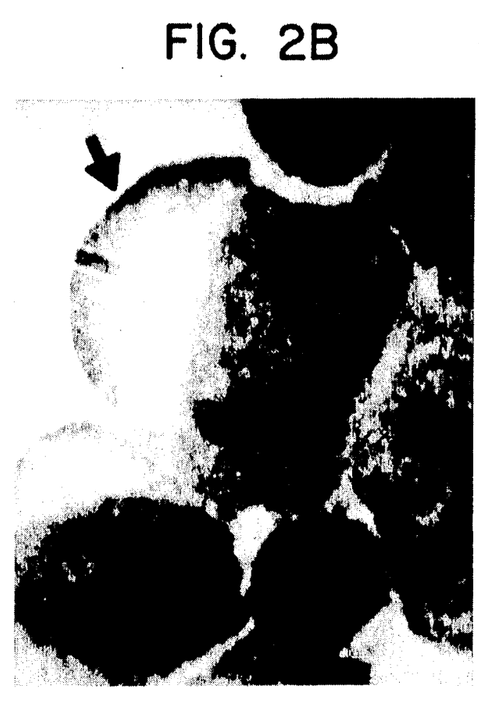

Visual inspection revealed an easily recognizable change in cellular morphology occuring as early as 4-6 hours after the onset of CT exposure. Sensitive cells displayed a loss of membrane blebs with an overall smoothing of their cell surface (See FIG. 2). This phenomenon persisted until the fourth or fifth day of exposure at which time cell lysis was noted to occur. However, up until that time cells remained viable as judged by trypan blue exclusion (data not shown).

The ability to stimulate adenylate cyclase and the generation of intracellular cAMP is the biologic effect of CT taught in the prior art, and was believed to be involved in the phenomena reported here. A rapid elevation in [cAMP] i was observed in response to 1 mg/ml of Ct. This response in NCI-H345, reached a maximum after 1 hour and returned to baseline within 6 hours. The same profile was not reliable reproduced by treating the cells with forskolin up to 10 mM, although neither forskolin at these concentrations nor dibutyryl cAMP at concentrations up to 1 mM affected the growth of SCLC in vitro (data not shown). In addition, previous studies had shown that the cAMP analogs dibutyryl cAMP and 8-Cl-cAMP did not inhibit signal transductions mediated by GRP. Taken together, these data argue that the transient elevation of cAMP caused by CT does not per se lead to inhibition of SCLC cell growth.

CT Substrates in SCLC

Figure 3A:
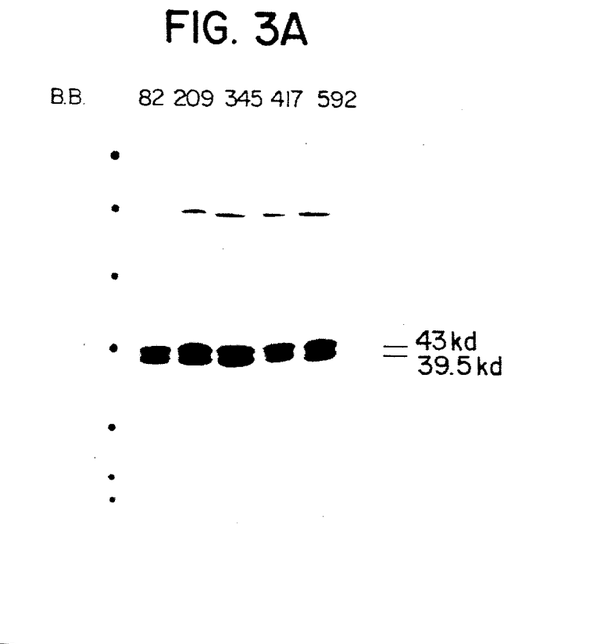
Figure 3B:
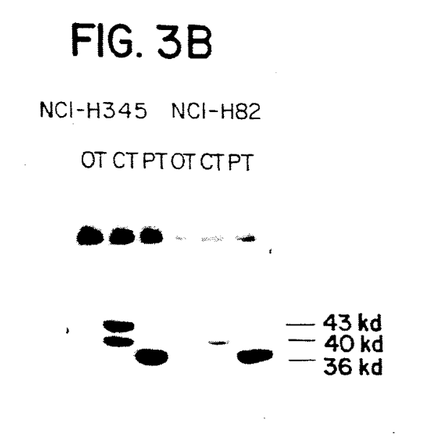
Figure 3C:
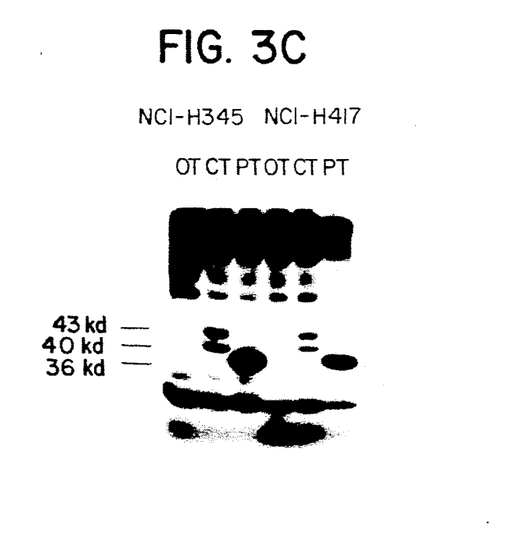

Since a frequently observed intracellular substrate for ADP-ribosylation by CT is Gs, the stimulatory G-protein of adenylate cyclase, it is possible that a decreased expression of this entity could explain differential cytotoxicity. Previous studies have shown two forms of Gs exist, due to alternative splicing of a single primary transcript. Utilizing an anti-Gs antibody, Western blots of membrane proteins from SCLC demonstrate no difference in the expression of Gs in CT-sensitive or resistant SCLC (FIG. 3A). These proteins co-migrate with authentic Gs prepared from brain. FIG. 3B and 3C demonstrate that membranes incubated in vitro with [$^{32}P$]-NAD and activated CT undergo ADP-ribosylation of substrates with very similar mobility in SDS-PAGE, and that there is no difference in the expression of these species between CT-sensitive and resistant SCLC. No other CT dependent ADP-ribosylation substrates were identified by modifying the GTP or NAD concentrations during the incubations or prolonging the incubations for up to 4 hours (data not shown).

In experiments not shown here, antibodies directed against $G_{i1}$, $G_{i2}$, $G_{i3}$, and $G_o$ revealed universal and uniform expression of these other G-proteins in the four SCLC cell lines studied. Thus, differential inhibition of SCLC cell growth by CT does not appear to relate to the absence or enhanced expression of Gs or of other known G proteins.

Figure 4:
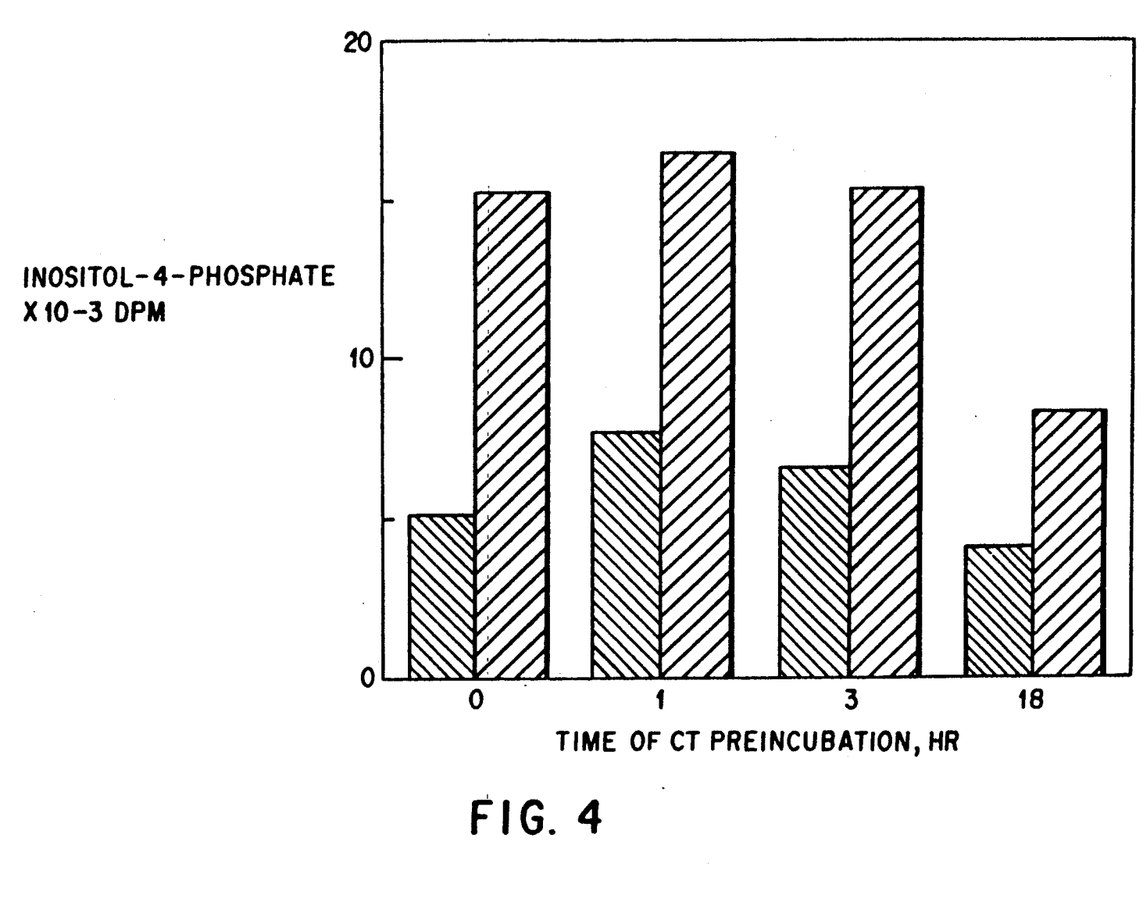
FIG. 4 Time course of CT effect on T4B induced inositol 4 phosphate formation. The inhibitory effect of CT is seen only beyond 3 hours of incubation.

It was found CT inhibition of Grp mediated signals in SCLC are dissociated from receptor affector coupling. Previous studies had demonstrated that CT inhibits the increase in [$Ca^{2+}$]$_i$ caused by bombesin agonists including GRP in SCLC, and that this inhibition was associated with a decreased capacity of the cells to increase phosphatidylinositol turnover after treatment with the peptide. FIG. 4 shows that in contrast to the increase of c-AMP observed in response to CT, inhibition of 100 nM [Tyr$^4$]-bombesin-induced increases of inositol-4-monophosphate (I-4-P) after 30 minutes of incubation with the peptide is not apparent in the first three hours of toxin treatment. Rather, inhibition is seen in this experiment only after 18 hours incubation with the toxin, in contrast to the maximal effect on Gs which is apparent after one hour.

Figure 5:
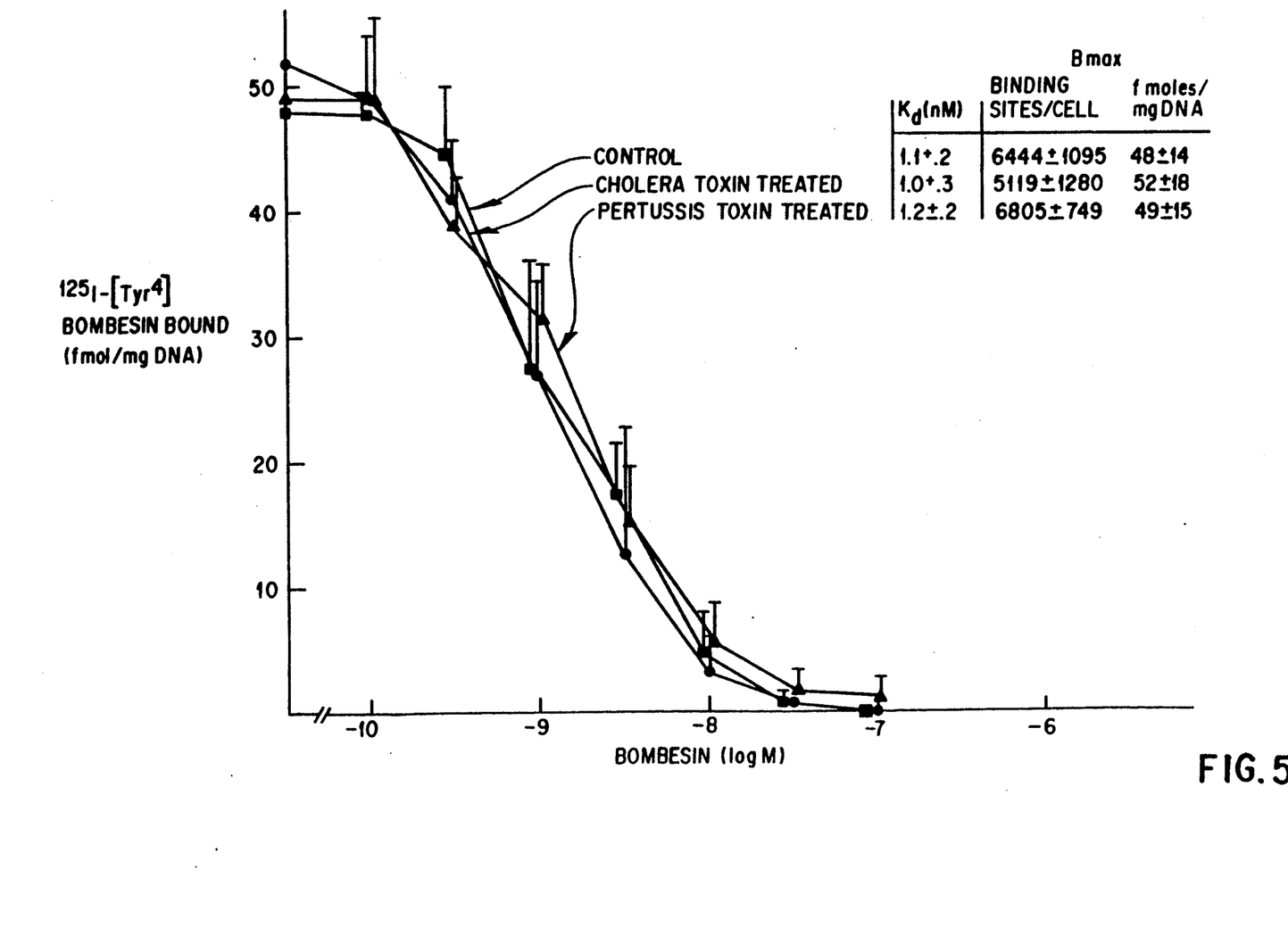
FIG. 5 Effect of bacterial toxin pretreatment on 125I-[Tyr4] bombesin. The binding of bombesin is unaffected by pretreatment of the cells with pertussis toxin or cholera toxin in conditions similar to those yielding inhibition of bombesin stimulated signal transduction.

It has been shown in other systems that the GRP receptor is coupled to a G protein, as evidenced by the decreased binding affinity observed in the presence of GTP analogues. However, in these systems, GRP binding was not sensitive to bacterial toxins. Similarly, incubation of NCI-H345 with PT, or CT in conditions identical to those inhibiting GRP mediated signal transduction pathways, did not result in any change in the binding characteristics of GRP to this cell line (see FIG. 5). This shows that, as in other tissues, the G protein coupling the GRP receptor of SCLC to its effector is not a toxin substrate, and that the CT dependent cytotoxicity and inhibition of GRP stimulated signals observed in SCLC cannot be simply accounted for by inhibition of receptor-effector coupling.

Figure 6:
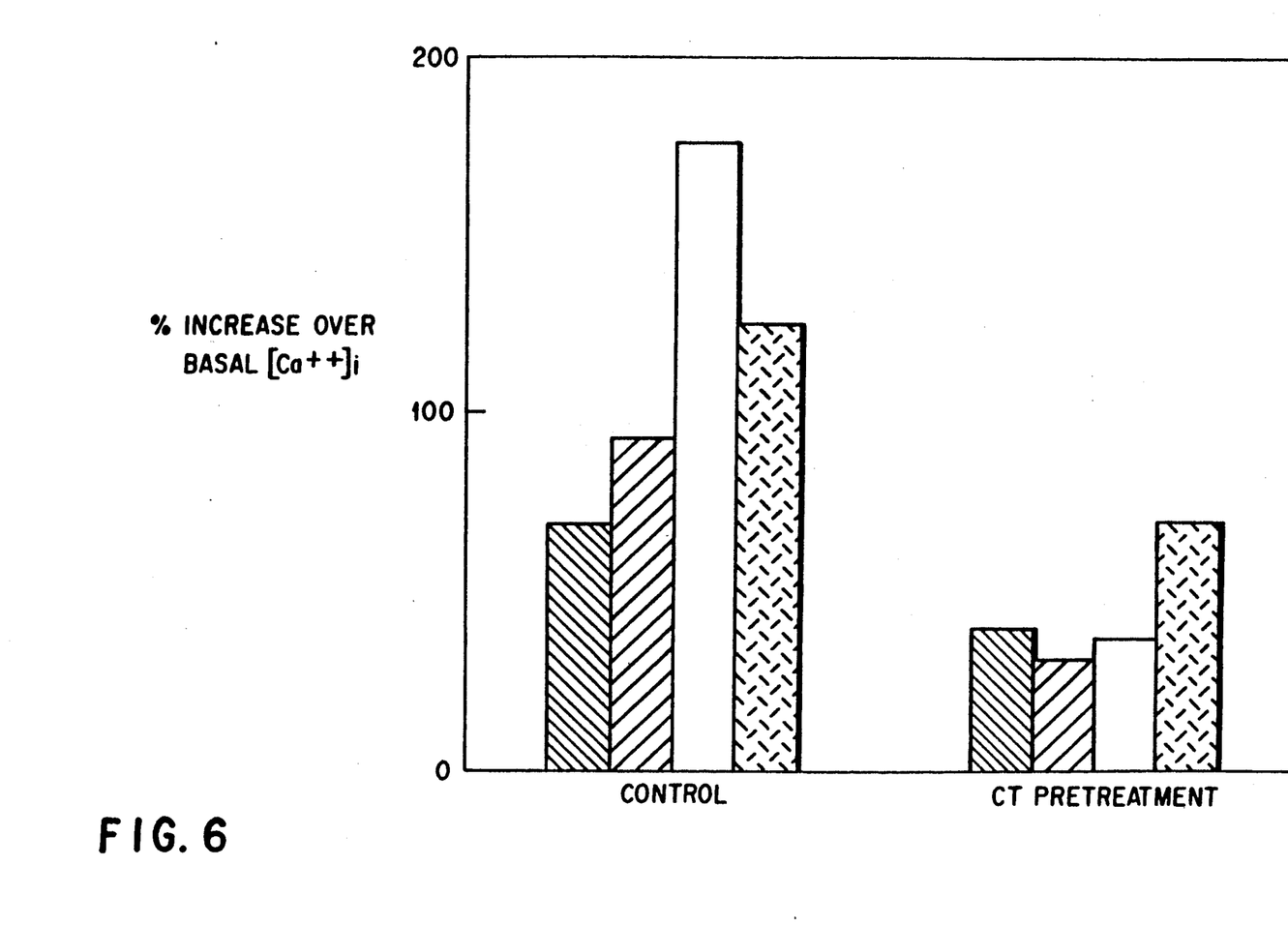
Figure 7A:
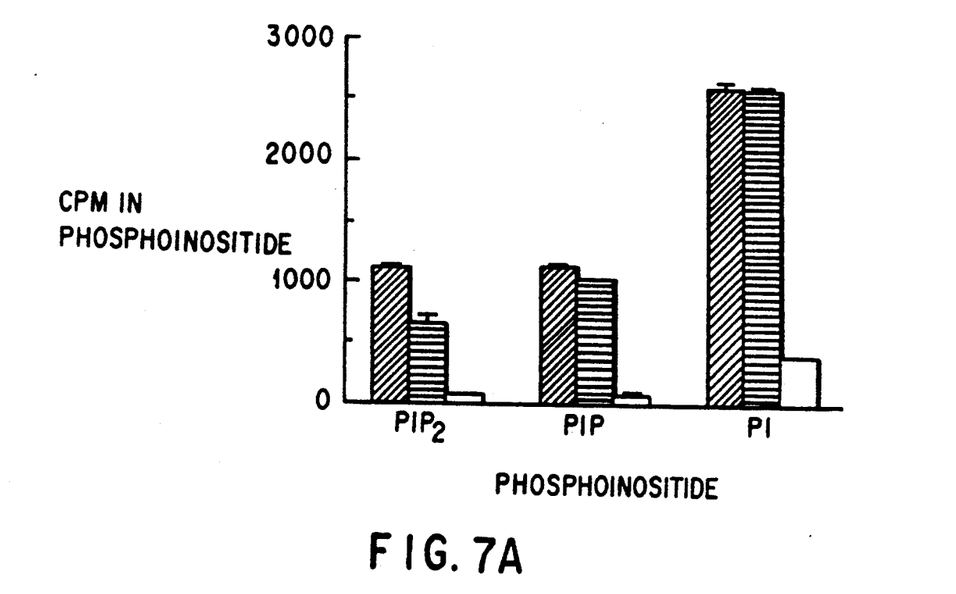
Figure 7B:
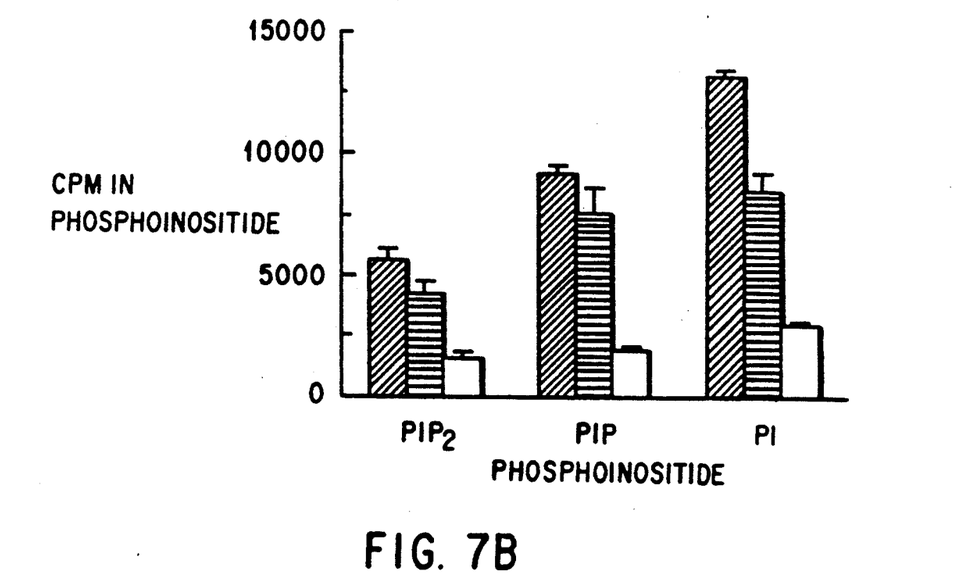
Figure 7C:
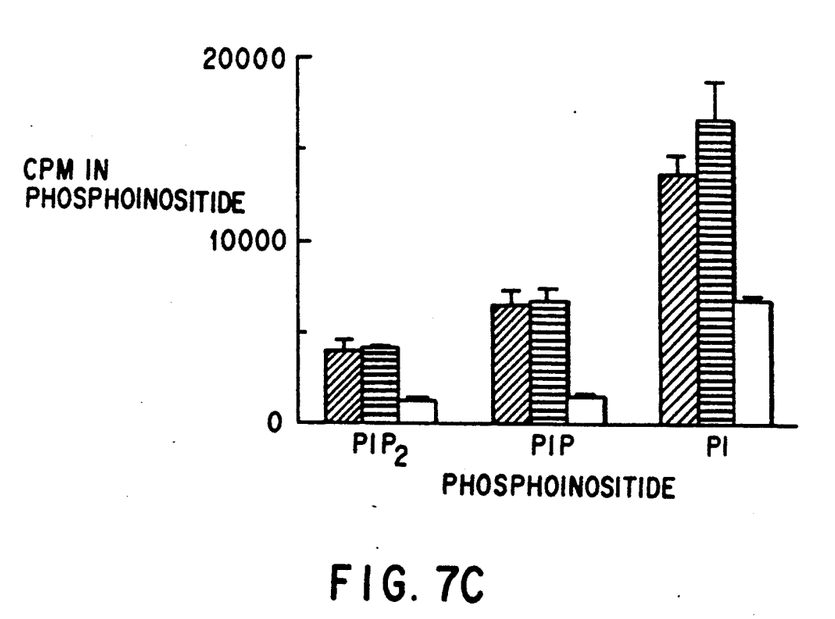
Figure 7D:
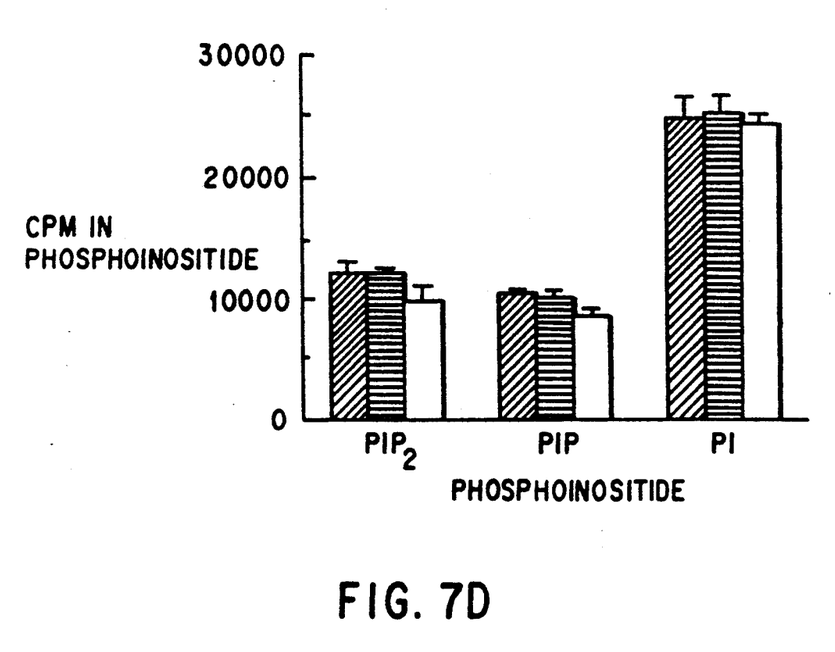

The signal transduction effects of CT are not specific to GRP. FIG. 6 demonstrates that incubation of SCLC with CT at 1 ug/ml for 18 hours results in a substantial inhibition of the intracellular calcium transient in response to GRP, AVP and serum.

FIGS. 7, A, B, and C demonstrate that pretreatment with 1 ug/ml of CT (but not the isolated b-subunit of CT) for 18 hours causes marked inhibition of the incorporation of [$^{32}PO_4$] into PI, PIP, and $PIP_2$ in the CT-sensitive SCLC cell lines NCI H-345, NCI H-209, and NCI H-82. NCI N-417 (FIG. 7D), insensitive to the growth inhibitory effects of the toxin, showed no inhibition of lipid precursor synthesis by the toxin.

Inhibition of cell replication by CT was, found in 9/11 SCLC cell lines, 1/5 NSCLC, and 1/1 colon carcinoma cell line with neuro-endocrine features. In contrast, 0/2 ovarian carcinoma cell line and the two hematopoietic cell lines HL-60 and Hut-78 were resistant to CT. In total, 11/21 human cancer cell lines tested to date showed growth inhibition by CT. Moreover, two rodent models have shown in vivo tumor regression after parenteral administration of CT with no detectable host toxicity.

In view of the discovery that the cholera toxin is effective only in instances where the malignant cells carry the $G_{M1}$ protein on the cell membrane, the method of treating patients with CT requires two procedures: (1) Testing the malignant tissue obtained from the patient for presence of $G_{M1}$ on the cells and (2) administering the cholera toxin in amounts sufficient to inhibit and/or kill malignant cells. In view of the discovery the selective action of CT, it is clearly not possible to predict, without determining the presence or absence of the $G_{M1}$ protein whether or not administration of cholera toxin in any amount will benefit the patient.

The dosage appropriate for any individual patient will vary according to size, age, and general condition. However, the dosage range is about 1 to 100 ug/Kg./day. The preferred dosage is about 5 to 40 ug/Kg/day. The toxin can be given parenterally. For treatment of peritonel maligancies, the medicinal compositions may be given directly into the peritoneal cavity. Bronchial lesions may be treated by administration of active ingredients by inhalation. However, administration into the gastro-intestinal tract is not advised because the toxin would probably be destroyed in the stomach, and such toxin as might reach the upper intestinal tract would cause diarrhea, the most common symptom of cholera. However, when the toxin is given in accord with the method taught herein, toxic effects are minimal.

The patient tissue obtained by any method such as washing or biopsy can be exposed to the bets subunit of CT conjugated to a label such as peroxidase. While the examples recited washed cells, the tissue need only be exposed to the labeled beta subunit of CT. If the binding assay indicates presence of $G_{M1}$, the patient should be treated with CT by the described method. If there is no evidence of binding, the patient is not a candidate for treatment with the cholera toxin.

We claim:

1. A method of treating malignancies comprising the steps of:
   A) Subjecting malignant tissue from the patient to labelled beta subunit of cholera toxin;
   B) Evaluating presence or absence of binding of labelled beta subunit to GM1 ganglioside;
   C) If binding of the labelled subunit to the tissue is positive, administering to the patient a malignancy-inhibiting effective amount of cholera toxin.

2. A method of claim 1 wherein the toxin is given parenterally at a dosage range of 5 to 100 ug/Kg per day.

3. A method of claim 1 wherein the cholera toxin is administered directly into the peritoneal cavity.

4. A method of claim 1 wherein the beta subunit of cholera toxin is conjugated to horseradish peroxidase.

* * * * *